United States Patent
Ceulemens et al.

(10) Patent No.: US 9,610,260 B2
(45) Date of Patent: *Apr. 4, 2017

(54) METHOD FOR THE TREATMENT OF DRAVET SYNDROME

(71) Applicants: THE KATHOLIEKE UNIVERSITEIT LEUVEN, Leuven (BE); UNIVERSITY HOSPITAL ANTWERP, Edegem (BE)

(72) Inventors: Berten Ceulemens, Westmalle (BE); Lieven Lagae, Edegem (BE)

(73) Assignees: The Katholieke Universiteit Leuven, Leuven (BE); University Hospital Antwerp, Edegem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,253

(22) Filed: Jul. 30, 2014

(65) Prior Publication Data

US 2014/0343161 A1    Nov. 20, 2014

Related U.S. Application Data

(62) Division of application No. 13/887,014, filed on May 3, 2013, now Pat. No. 9,549,909.

(51) Int. Cl.

| | | |
|---|---|---|
| *A61K 31/135* | (2006.01) | |
| *A61K 31/137* | (2006.01) | |
| *A61K 45/06* | (2006.01) | |
| *A61K 31/19* | (2006.01) | |
| *A61K 31/36* | (2006.01) | |
| *A61K 31/5513* | (2006.01) | |

(52) U.S. Cl.
CPC .......... *A61K 31/137* (2013.01); *A61K 31/135* (2013.01); *A61K 31/19* (2013.01); *A61K 31/36* (2013.01); *A61K 31/5513* (2013.01); *A61K 45/06* (2013.01)

(58) Field of Classification Search
CPC ......................... A61K 31/137; A61K 2300/00
See application file for complete search history.

(56) References Cited

FOREIGN PATENT DOCUMENTS

JP    H05-310564 A    11/1993

OTHER PUBLICATIONS

Muelly et al., Human Mutation, 25:535-542, 2005.*
Remington, The Science and Practice of Pharmacy, Nineteenth Edition—1995, pp. 710-712; pp. 1495-1497, 1506.*
Ceulemans et al., "Successful use of fenfluramine as an add-on treatment for Dravet syndrome" Epilepsia, 53(7), 2012, 1131-1139.
Casaer et al., "Fenfluramine as a Potential Antiepileptic Drug" Epilepsia, 43(2), 205-206, 2002.
Ceulemans, "Overall management of patients with Dravet syndrome" Developmental Medicine & Child Neurology, 2011, 53, 19-23.
Brunklaus et al., "Prognostic, clinical and demographic features in SCN1A mutation-positive Dravet syndrome" Brain, 2012, p. 1-8.
Casaer et al., "Add-on Therapy of Fenfluramine in Intractable Self-Induced Epilepsy" Neuropaediatrics 1996, 27(4):171-173.
K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).
Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).
Remington, "The Science and Practice of Pharmacy", Nineteenth Edition (1995), pp. 710-712.
Clemens B., "Dopamine agonist treatment of self-induced pattern-sensitive epilepsy. A case Report" Epilepsy Res. 2. 1988, p. 340-343.
Ceulemans B., "Successful Use of Fenfluramine as Add-On Treatment in Dravet Syndrome" Epilepsia, 52(Suppl. 6):4-22 (2011).

* cited by examiner

*Primary Examiner* — Shobha Kantamneni
(74) *Attorney, Agent, or Firm* — Karl Bozicevic; Bozicevic, Field & Francis LLP

(57) ABSTRACT

A method of treating and/or preventing Dravet Syndrome in a patient such as a patient previously diagnosed with Dravet Syndrome, by administering an effective dose of fenfluramine or its pharmaceutically acceptable salt to that patient. Dravet Syndrome patients are typically children under the age of 18 and are treated at a preferred dose of less than about 0.5 to about 0.01 mg/kg/day.

6 Claims, No Drawings

METHOD FOR THE TREATMENT OF DRAVET SYNDROME

BACKGROUND ART

This invention relates to the treatment of Dravet Syndrome using an amphetamine derivative, specifically fenfluramine.

Fenfluramine, i.e. 3-trifluoromethyl-N-ethylamphetamine is an amphetamine derivative having the structure:

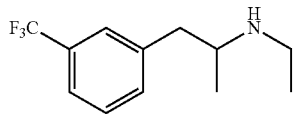 [SMILES: CCNC(C)Cc1cccc(C(F)(F)F)c1]

Fenfluramine was first marketed in the US in 1973 and had been administered in combination with phentermine to prevent and treat obesity. However, in 1997, it was withdrawn from the US market as its use was associated with the onset of cardiac fibrosis and pulmonary hypertension. Subsequently, the drug was withdrawn from sale globally and is no longer indicated for use in any therapeutic area.

Despite the health concerns surrounding fenfluramine, attempts have been made to identify further therapeutic uses for that product. Aicardi and Gastaut (*New England Journal of Medicine* (1985), 313:1419 and *Archives of Neurology* (1988) 45:923-925) reported four cases of self-induced photosensitive seizures that responded to treatment with fenfluramine.

Clemens, in *Epilepsy Research* (1988) 2:340-343 reported a study on a boy suffering pattern sensitivity-induced seizures that were resistant to anticonvulsive treatment. Fenfluramine reportedly successfully terminated these self-induced seizures and the author concluded that this was because fenfluramine blocked the photosensitive triggering mechanism.

In *Neuropaediatrics*, (1996); 27(4):171-173, Boel and Casaer reported on a study on the effects of fenfluramine on children with refractory epilepsy. They concluded that when fenfluramine was administered at a dose of 0.5 to 1 mg/kg/day, this resulted in a reduction in the number of seizures experienced by the patients.

In a letter to *Epilepsia*, published in that journal (*Epilepsia*, 43(2):205-206, 2002), Boel and Casaer commented that fenfluramine appeared to be of therapeutic benefit in patients with intractable epilepsy.

Epilepsy is a condition of the brain marked by a susceptibility to recurrent seizures. There are numerous causes of epilepsy including, but not limited to birth trauma, perinatal infection, anoxia, infectious diseases, ingestion of toxins, tumours of the brain, inherited disorders or degenerative disease, head injury or trauma, metabolic disorders, cerebrovascular accident and alcohol withdrawal.

There are a large number of subtypes of epilepsy that have been characterised. For example, the following list of conditions are set out in *Meritt's Neurology* (12th Edition):

I. Idiopathic epilepsy syndromes (focal or generalised)
   A. Benign neonatal convulsions
      1. Familial
      2. Nonfamilial
   B. Benign childhood epilepsy
      1. With central-midtemporal spikes
      2. With occipital spikes
   C. Childhood/juvenile absence epilepsy
   D. Juvenile myoclonic epilepsy (including generalised tonic-clonic seizures on awakening)
   E. Idiopathic epilepsy, otherwise unspecified II. Symptomatic epilepsy syndromes (focal or generalised)
   A. West syndrome (infantile spasms)
   B. Lennox-Gastaut syndrome
   C. Early myoclonic encephalopathy
   D. Epilepsia partialis continua
      1. Rasmussen syndrome (encephalitic form)
      2. Restricted form
   E. Acquired epileptic aphasia (Landau-Kleffner syndrome)
   F. Temporal lobe epilepsy
   G. Frontal lobe epilepsy
   H. Posttraumatic epilepsy
   I. Other symptomatic epilepsy, focal or generalised, not specified III. Other epilepsy syndromes of uncertain or mixed classification
   A. Neonatal seizures
   B. Febrile seizures
   C. Reflex epilepsy
   D. Other unspecified As can be seen from, for example, Part III of that list, there are still subtypes of epilepsy that have not yet been fully characterised and thus, the list is far from complete.

Those skilled in the art will recognize that these subtypes of epilepsy are triggered by different stimuli, are controlled by different biological pathways and have different causes, whether genetic or environmental. In other words, the skilled artisan will recognize that teachings relating to one epileptic subtype are not necessarily be applicable to other subtypes. This can include recognition that different epilepsy subtypes respond differently to different anticonvulsant drugs.

Dravet Syndrome is a rare and catastrophic form of intractable epilepsy that begins in infancy. Initially, the patient experiences prolonged seizures. In their second year, additional types of seizure begin to occur and this typically coincides with a developmental decline, possibly due to repeated cerebral hypoxia. This leads to poor development of language and motor skills.

Children with Dravet Syndrome are likely to experience multiple seizures per day. Epileptic seizures are far more likely to result in death in sufferers of Dravet Syndrome; approximately 10 to 15% of patients diagnosed with Dravet Syndrome die in childhood, particularly between two and four years of age. Additionally, patients are at risk of numerous associated conditions including orthopedic developmental issues, impaired growth and chronic infections.

Of particular concern, children with Dravet Syndrome are particularly susceptible to episodes of CFV. This severe and intractable condition is categorized as a medical emergency requiring immediate medical intervention, typically involving hosptialisation. Status Epilepticus can be fatal. It can also be associated with cerebral hypoxia, possibly leading to damage to brain tissue. Frequent hospitalizations of children with Dravet Syndrome are clearly distressing, not only to the patient but also to family and carers.

The cost of care for Dravet Syndrome patients is also high as the affected children require constant supervision and many require institutionalisation as they reach teenage years.

At present, although a number of anticonvulsant therapies can be employed to reduce the instance of seizures in patients with Dravet Syndrome, the results obtained with such therapies are typically poor and those therapies only effect partial cessation of seizures at best. Seizures associated with Dravet Syndrome are typically resistant to conventional treatments. Further, many anticonvulsants such as clobazam and clonazepam have undesirable side effects, which are particularly acute in pediatric patients.

Stiripentol is approved in Europe but not in the US for the treatment of Dravet Syndrome. It does not exhibit an anticonvulsant activity in its own right; it acts by inhibiting the metabolism of other anticonvulsants thereby prolonging their activity. However, concerns remain regarding the use of stiripentol due to its inhibitory effect on hepatic cytochrome P450. Further, the interactions of stiripentol with a large number of drugs means that combination therapy (which is typically required for patients with Dravet Syndrome) is problematic.

There is accordingly a need to provide an improved method for treating or preventing Dravet Syndrome and/or for treating, preventing and/or ameliorating seizures experienced by sufferers of Dravet Syndrome.

BRIEF SUMMARY OF THE INVENTION

According to a first aspect of the present invention, there is provided a method of treating and/or preventing Dravet Syndrome in a patient comprising administering an effective dose of fenfluramine to that patient.

According to a further aspect of the present invention, there is provided a method of treating, preventing and/or ameliorating seizures in a patient diagnosed with Dravet Syndrome comprising administering an effective dose of fenfluramine to that patient.

According to a further aspect of the present invention, there is provided a method of treating a patient that exhibits a mutation in one or more of a gene selected from the group consisting of SCN1A, SCN1B, SCN2A, SCN3A, SCN9A, GABRG2, GABRD and PCDH19 by by administering to that patient an effective dose of fenfluramine.

A still further aspect of this invention contemplates a method for stimulating one or more 5-HT receptors in the brain of a patient by administering an effective dose of fenfluramine or a pharmaceutically acceptable salt thereof to that patient. Illustrative one or more 5-HT receptors are selected from the group consisting of one or more of $5\text{-HT}_1$, $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$ $5\text{-HT}_6$, and $5\text{-HT}_7$.

Yet another aspect of the invention contemplates coadministration of an effective dose of one or more co-therapeutic agents with the fenfluramine.

DETAILED DESCRIPTION OF THE INVENTION

After many years of extensive research, it has unexpectedly been found that fenfluramine can be used to treat, or at least minimiZe the effects of Dravet Syndrome. This is confirmed by the results presented herein, and also in the article by Ceulemans et al., *Epilepsia* (2012) 53(7):1131-1139, the contents of which are incorporated herein.

For the avoidance of doubt, the term "prevention" of seizures means the total or partial prevention (inhibition) of seizures. Ideally, the methods of the present invention result in a total prevention of seizures; indeed, this ideal has been achieved in a number of patients treated by the inventors. However, the invention also encompasses methods in which the instances of seizures are decreased by at least 50%, at least 60%, at least 70%, at least 80% or at least 90%.

It is known that patients with Dravet Syndrome commonly experience photosensitive or induced seizures. From teachings in the prior art, e.g. Aicardi and Gastaut (1988) and Boel and Casaer (1996)—both discussed above, it might have been expected that fenfluramine would reduce photosensitive or induced seizures. Importantly, however, it has surprisingly been found that all types of seizures exhibited by patients with Dravet Syndrome, that is seizures in addition to and other than those that are photosensitive or induced can be suppressed by treatment in accordance with a method of the present invention.

Thus, in context of the present invention, the term "seizure" is used to not only encompass photosensitive or induced seizures, but some or all of the other types of seizures experienced by epileptics, including but not limited to Status Epilepticus.

There are a number of genetic mutations that are indicative of Dravet Syndrome. Mutations in the SCN1A (such as partial or total deletion mutations, truncating mutations and/or missense mutations e.g. in the voltage or pore regions S4 to S6), SCN1B (such as the region encoding the sodium channel β1 subunit), SCN2A, SCN3A, SCN9A, GABRG2 (such as the region encoding the γ2 subunit), GABRD (such as the region encoding the δ subunit) and/or PCDH19 genes have been linked to Dravet Syndrome.

Thus, according to a further aspect of the present invention, there is provided a method of treating a patient that exhibits a mutation in one, some or all of the above genes by administering to that patient an effective dose of fenfluramine. In certain embodiments of this aspect of the invention, the patient has been diagnosed with Dravet Syndrome.

Fenfluramine has been known to inhibit serotonin reuptake and to trigger the release of serotonin in the brain due to disruption of its vesicular storage. However, until the present invention was made, it was not known that fenfluramine's mechanism of action made it suitable for the treatment of Dravet Syndrome.

Thus, according to a still further aspect of the present invention, there is provided a method of stimulating one or more 5-HT receptors in the brain of a patient by administering an effective dose of fenfluramine to said patient, said one or more 5-HT receptors being selected from one or more of $5\text{-HT}_1$, $5\text{-HT}_{1A}$, $5\text{-HT}_{1B}$, $5\text{HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$ $5\text{-HT}_6$, and $5\text{-HT}_7$ amongst others. In certain embodiments of this aspect of the invention, the patient has been diagnosed with Dravet Syndrome.

In embodiments of the invention, any effective dose of fenfluramine can be employed. However, surprisingly low doses of fenfluramine have been found by the inventors to be efficacious, particularly for inhibiting or eliminating seizures in Dravet Syndrome patients. Thus, in preferred embodiments of the invention, a daily dose of less than about 0.5 mg/kg/day, about 0.45 mg/kg/day, about 0.4 mg/kg/day, about 0.3 mg/kg/day, about 0.25 mg/kg/day or about 0.2 mg/kg/day to about 0.1 mg/kg/day, about 0.05 mg/kg/day, or about 0.01mg/kg/day is employed. Put differently, a preferred dose is less than about 0.5 to about 0.01 mg/kg/day. Such a dose is less than the daily dose of fenfluramine suggested for administraton to achieve weight loss.

The dose of fenfluramine administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms;

transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

The dosage form of fenfluramine employed in the methods of the present invention can be prepared by combining fenfluramine with one or more pharmaceutically acceptable diluents, carriers, adjuvants, and the like in a manner known to those skilled in the art of pharmaceutical formulation.

In a method of the present invention, fenfluramine can be employed as a monotherapy in the treatment of Dravet Syndrome. Alternatively, fenfluramine can be coadministered simultaneously, sequentially or separately with one or more co-therapeutic agents, such as anticonvulsants. Preferred co-therapeutic agents can be selected from the group consisting of carbamazepine, ethosuximide, fosphenytoin, lamotrigine, levetiracetam, phenobarbitol, progabide, topiramate, stiripentol, valproic acid, valproate, verapamil, and benzodiazepines such as clobazam, clonazepam, diazepam, ethyl loflazepate, lorazepam, midazolam. Use of a pharmaceutically acceptable salt of a co-therapeutic agent is also contemplated.

Fenfluramine can be administered in the form of the free base, or in the form of a pharmaceutically acceptable salt, for example selected from the group consisting of hydrochloride, hydrobromide, hydroiodide, maleate, sulphate, tartrate, acetate, citrate, tosylate, succinate, mesylate and besylate. Further illustrative pharmaceutically acceptable salts can be found in Berge et al., *J. Pharm Sci.* (1977) 68(1):1-19.

Fenfluramine for use in the methods of the present invention may be produced according to any pharmaceutically acceptable process known to those skilled in the art. Examples of processes for synthesizing fenfluramine are provided in the following documents: GB1413070, GB1413078 and EP441160.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents.

A method of the present invention can be practiced on any appropriately diagnosed patient. In a typical embodiment of the present invention, the patient is aged about 18 or less, about 16 or less, about 14 or less, about 12 or less, about 10 or less, about 8 or less, about 6 or less or about 4 or less to about 0 months or more, about 1 month or more, about 2 months or more, about 4 months or more, about 6 months or more or about 1 year or more. Thus, the diagnosed patient is typically about one month old to about 18 years old when treated.

The invention is further illustrated in the following Comparative Example.

COMPARATIVE EXAMPLE 1

The results of two pivotal studies (conducted in France and Italy) that led to approval of stiripentol in the European Union are provided below. In the first table, the number of test subjects who became seizure-free upon co-administration of stiripentol and either valproate or clobazam vs a placebo or two months is provided. In the second table, the number of subjects who exhibited a >50% reduction in the number of seizures following administration of stiripentol and either valproate or clobazam vs a placebo or two months is provided.

TABLE 1

Seizure Free Patients (Treated with Stiripentol and either Valproate or Clobazam vs Placebo)

| | Seizure Free Patients | |
|---|---|---|
| | Stiripentol | Placebo |
| STICLO-France | 9/20 (45%) | 0/16 (0%) |
| STICLO-Italy | 3/11 (27%) | 0/9 (0%) |
| Combined | 12/31 (38.7%) | 0/25 (0%) |

TABLE 2

Responders - >50% Reduction in the Number of Seizures (Treated with Stiripentol and either Valproate or Clobazam vs Placebo)

| | Responders | |
|---|---|---|
| | Stiripentol | Placebo |
| STICLO-France | 15/21 (71.4%) | 1/20 (5%) |
| STICLO-Italy | 8/12 (66.7%) | 1/11 (9.1%) |
| Combined | 23/33 (69.7%) | 2/31 (6.5%) |

The following table provides results based on the data presented in Ceulemans et al., *Epilepsia* (2012) 53(7):1131-1139. Patients were administered an average daily dose of fenfluramine of 0.34 mg/kg/day for between 1 and 22 years.

TABLE 3

Seizure Free Patients and Responders (Treated with Fenfluramine and Valproate) Fenfluramine

| Seizure-free Patients | >50% Reduction in Seizures |
|---|---|
| 8/12 (66%) | 9/12 (75%) |

As can be seen from the foregoing data, long-term fenfluramine treatment advantageously resulted in a seizure-free condition in 66.6% of test subjects, compared to 38.7% for stiripentol.

Additionally, long-term fenfluramine treatment advantageously resulted in a slightly improved reduction in seizures (75%) as compared to the reduction in seizures in patients treated with stiripentol for two months (69.7%).

These results confirm that fenfluramine provides long term elimination/reduction in seizures to a greater extent than observed with short term administration of the currently approved therapy (in the EU), stiripentol.

These results were achieved, in the vast number of cases, using significantly lower doses of fenfluramine than those proposed previously in the treatment of various conditions typified by seizures. Additionally and surprisingly, fenfluramine effectively reduced the incidence of all types of seizures and not only photosensitive or self-induced seizures.

The subjects treated with fenfluramine were monitored using echocardiography for possible heart valve defects. No clinically relevant defects were identified.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method of treating seizures in a patient diagnosed with Dravet syndrome and exhibiting a mutation in one, some or all of the genes selected from the group consisting of SCN1A, SCN1B, SCN2A, SCN3A, SCN9A, GABRG2, GABRD and PCDH19 comprising administering to said patient an effective dose of fenfluramine or a pharmaceutically acceptable salt thereof;
   administering an effective dose of stiripentol or a pharmaceutically acceptable salt thereof to said patient;
   administering an effective dose of a valproate or a pharmaceutically acceptable salt thereof to said patient; and
   administering an effective dose of clobazam or a pharmaceutically acceptable salt thereof to said patient,
   whereby seizures are ameliorated in the patient exhibiting the mutation.

2. The method of claim 1, wherein the effective dose of fenfluramine is 0.5 mg/kg/day to 0.01 mg/kg/day.

3. The method of claim 2, wherein said patient is age 18 or less.

4. A method of treating seizures in a patient diagnosed with Dravet syndrome, comprising:
   orally administering to said patient an effective dose of a liquid formulation comprising fenfluramine or a pharmaceutically acceptable salt thereof;
   administering an effective dose of stiripentol or a pharmaceutically acceptable salt thereof to said patient;
   administering an effective dose of a valproate or a pharmaceutically acceptable salt thereof to said patient; and
   administering an effective dose of clobazam or a pharmaceutically acceptable salt thereof to said patient,
   whereby seizures are ameliorated in the patient exhibiting the mutation,
   wherein the patient exhibits a mutation in one, some or all of the genes selected from the group consisting of SCN1A, SCN1B, SCN2A, SCN3A, SCN9A, GABRG2, GABRD and PCDH19, and has been diagnosed with Dravet Syndrome.

5. The method of claim 4, wherein the effective dose of fenfluramine is 0.5mg/kg/day to 0.01 mg/kg/day.

6. The method of claim 4, wherein the patient is age 18 or less.

* * * * *